(12) United States Patent
Kim et al.

(10) Patent No.: US 10,464,050 B2
(45) Date of Patent: Nov. 5, 2019

(54) DEHYDRATION CATALYST FOR PREPARING N-SUBSTITUTED MALEIMIDE, PREPARATION METHOD THEREOF, AND METHOD OF PREPARING N-SUBSTITUTED MALEIMIDE

(71) Applicant: LG CHEM, LTD., Seoul (KR)

(72) Inventors: Ji Yeon Kim, Daejeon (KR); Jun Seon Choi, Daejeon (KR); Joo Young Cheon, Daejeon (KR); Wang Rae Joe, Daejeon (KR); Kyung Soo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/091,091

(22) PCT Filed: Aug. 1, 2017

(86) PCT No.: PCT/KR2017/008296
§ 371 (c)(1),
(2) Date: Oct. 3, 2018

(87) PCT Pub. No.: WO2018/038415
PCT Pub. Date: Mar. 1, 2018

(65) Prior Publication Data
US 2019/0118168 A1    Apr. 25, 2019

(30) Foreign Application Priority Data

Aug. 24, 2016 (KR) .................. 10-2016-0107851
Jul. 31, 2017 (KR) .................. 10-2017-0097281

(51) Int. Cl.
| | | |
|---|---|---|
| B01J 27/16 | (2006.01) | |
| B01J 37/03 | (2006.01) | |
| C07D 207/448 | (2006.01) | |
| B01J 37/04 | (2006.01) | |
| B01J 37/08 | (2006.01) | |
| B01J 37/06 | (2006.01) | |

(52) U.S. Cl.
CPC ............ B01J 27/16 (2013.01); B01J 37/031 (2013.01); B01J 37/04 (2013.01); B01J 37/06 (2013.01); B01J 37/08 (2013.01); C07D 207/448 (2013.01)

(58) Field of Classification Search
CPC ...................................................... B01J 27/16
See application file for complete search history.

(56) References Cited

U.S. PATENT DOCUMENTS

| | | | |
|---|---|---|---|
| 4,851,547 A | 7/1989 | Kita et al. | |
| 4,980,483 A | 12/1990 | Kita et al. | |
| 5,068,357 A * | 11/1991 | Tsumura | C07D 207/448 548/521 |
| 5,068,537 A | 11/1991 | Tsumura et al. | |
| 5,175,309 A * | 12/1992 | Tsumura | C07D 207/448 548/521 |
| 5,602,205 A | 2/1997 | Singh et al. | |
| 8,283,477 B2 * | 10/2012 | Kim | C07D 207/448 548/451 |
| 2003/0105337 A1 | 6/2003 | Wu et al. | |
| 2011/0124882 A1 | 5/2011 | Kim et al. | |

FOREIGN PATENT DOCUMENTS

| | | |
|---|---|---|
| CA | 906494 A | 8/1972 |
| DE | 2100800 A1 | 7/1971 |
| EP | 3421451 A1 | 1/2019 |
| GB | 1041027 A | 9/1966 |
| JP | 47-024024 B2 | 7/1972 |
| JP | S5849338 A | 3/1983 |
| JP | H021476 A | 1/1990 |
| JP | 2004-175711 A | 6/2004 |
| JP | 4014683 B2 | 11/2007 |
| JP | 2009126866 A | 6/2009 |
| JP | 4991471 B2 | 8/2012 |
| JP | 5101821 B2 | 12/2012 |
| KR | 10-0053080 B1 | 7/1992 |
| KR | 10-2009-0054494 A | 6/2009 |
| KR | 10-2009-0069016 A | 6/2009 |
| KR | 10-0923536 B1 | 10/2009 |
| KR | 10-2016-0005358 A | 1/2016 |

OTHER PUBLICATIONS

Cheng et al., "High performance mesoporous zirconium phosphate for dehydration of xylose to furfural in aqueous-phase", journal, Oct. 2013, p. 23228-23235, vol. 3, RSC Advances, The Royal Society of Chemistry, Nanjing University, Nanjing, China.
Search Report dated Apr. 25, 2019 for European Application No. 17843835.4.
Kamiya et al., "Zirconium phosphate with a high surface area as a water-tolerant solid acid", Catalysis Letters, Apr. 2004, p. 45-47, vol. 94, Graduate School of Earth Science, Hokkaido University, Sapporo, Japan.
Huimei Gan et al., "Gas phase dehydration of glycerol to acrolein catalyzed by zirconium phosphate", Chinese Journal of Catalysis, 2014, p. 1148-1156, vol. 35, No. 7, Elsevier B.V.
International Search Report for PCT/KR2017/008296 filed on Aug. 1, 2017.
Lester E. Coleman, Jr. et al., "Reaction of Primary Aliphatic Amines with Maleic Anhydride", J. Org. Chem., Jan. 1959, p. 135-136, vol. 24.
M.P. Cava et al., "N-Phenylmaleimide", Organic Syntheses Coll., 1973, p. 944, vol. 5, Organic Syntheses, Inc.

* cited by examiner

Primary Examiner — Golam M Shameem

(57) ABSTRACT

A dehydration catalyst for preparing N-substituted maleimide, which may minimize formation of by-products, is reusable because its activity is not reduced significantly even after being reused several times, and may maintain its reaction activity for a long time, a preparation method thereof, and a method of preparing N-substituted maleimide, are provided.

13 Claims, No Drawings

DEHYDRATION CATALYST FOR PREPARING N-SUBSTITUTED MALEIMIDE, PREPARATION METHOD THEREOF, AND METHOD OF PREPARING N-SUBSTITUTED MALEIMIDE

CROSS-REFERENCE TO RELATED APPLICATIONS

The present application is a U.S. National Stage of PCT/KR2017/008296, filed Aug. 1, 2017, which is based on, and claims priority from, Korean Patent Application Nos. 10-2016-0107851 and 10-2017-0097281, filed on Aug. 24, 2016 and Jul. 31, 2017, respectively, the disclosures of which are hereby incorporated by reference herein in their entirety.

TECHNICAL FIELD

The present invention relates to a dehydration catalyst for preparing N-substituted maleimide, which minimizes formation of by-products, is reusable because its activity is not reduced even after being reused several times, and maintains its reaction activity for a long time, a preparation method thereof, and a method of preparing N-substituted maleimide.

BACKGROUND OF THE INVENTION

N-substituted maleimides are widely used as raw materials or intermediates for pharmaceuticals, agricultural chemicals, dyes, and polymer compounds. In particular, N-substituted maleimides are useful as monomers or intermediates for polymer compounds or synthetic products, and are widely used as monomers for improving heat resistance of styrene-based resins.

Various methods of preparing N-substituted maleimides are known. For example, a method of obtaining N-substituted maleimides by heating maleic acid monoamides (maleamic acids), which are easily obtainable from maleic anhydride and amines such as butylamine, octylamine, decylamine and dodecylamine, to 180° C. for effective dehydrocyclization (L. E. Coleman et al., J. Org. Chem., 24, 135(1959)) is known.

However, this method cannot be used in practice since it gives a low yield of only 15% to 50% and moreover yields a large amount of polymers of a polyamide structure as a by-product.

A known laboratory preparation method is to react maleic anhydride and aniline in the presence of a sodium acetate catalyst using a dehydrating agent such as acetic anhydride (Org. Synth. Coll., 1973, Vol. 5, page 944). Although this method gives N-substituted maleimides in a relatively high yield (75% to 80%), it has a disadvantage of high production cost since it requires the use of a stoichiometric amount of acetic anhydride, which results in additional cost of an auxiliary material.

On the other hand, dehydrocyclization of maleic acid monoamides under milder conditions using an effective dehydration catalyst without using dehydrating agents is more commercially effective. Various attempts have been made regarding such a process. There have been known, for example, a method of using a basic catalyst such as an alkali metal acetate, sodium hydroxide, or triethylamine as a catalyst (Japanese Patent Application Publication No. JP 1972-024024 B2, Canadian Patent Publication No. CA 906494 A, and German Patent Publication No. DE 02100800 A1) and a method of using an acidic catalyst such as sulfuric acid and a sulfonic acid (British Patent Publication No. GB 001041027 A). However, these methods of using such catalysts are not yet fully satisfactory in suppressing side reactions since they give polymeric products as by-products. Moreover, there is a problem that these methods require complicated steps in separation and recovery of the catalyst and removal of by-products from reaction products.

As described above, the prior art dehydrocyclization of maleic acid monoamides in the presence of a catalyst gives a relatively large amount of polymeric side-reaction products, and consequently, has drawbacks in yield, product purity, and operation procedures. Thus, suppression of the polymeric side-reaction products has become an important problem to be solved. Further, existing phosphoric acid-supported catalysts are disadvantageous in that a large amount of phosphoric acid-based components are eluted when the catalyst are reused, and as a result, their activity is drastically reduced and side reactions are greatly promoted. There is also a problem that the phosphoric acid-supported catalyst should be added periodically to maintain its reaction activity, in order to maintain the reaction for a long time.

Accordingly, it is necessary to develop a catalyst which may minimize formation of by-products during preparation of N-substituted maleimide, is reusable because its activity is not reduced even after being reused several times, and may maintain its reaction activity for a long time.

DETAILS OF THE INVENTION

Objects of the Invention

The present invention provides a dehydration catalyst for preparing N-substituted maleimide, which may minimize formation of by-products, is reusable because its activity is not reduced even after being reused several times, and may maintain its reaction activity for a long time.

Further, the present invention provides a method of preparing the dehydration catalyst for preparing N-substituted maleimide.

Furthermore, the present invention provides a method of preparing N-substituted maleimide in the presence of the above catalyst.

Means for Achieving the Object

According to one embodiment of the present invention, a dehydration catalyst for preparing N-substituted maleimide, which is represented by the following Formula 1 is provided.

$$Zr_x(H_aPO_b)_c \qquad \text{[Formula 1]}$$

In Formula 1, x is 0.5 to 1.5, a and b are each independently 0 to 8, and c is 1 to 4.

For example, in the catalyst of Formula 1, c/x may be 1.5 to 2.67.

According to another embodiment of the present invention, a method of preparing the dehydration catalyst for preparing N-substituted maleimide is provided, the method including the step of precipitating the catalyst represented by Formula 1 by mixing a zirconium precursor and a phosphate compound.

The step of precipitating the catalyst may include stirring the mixture containing the zirconium precursor and the phosphate compound at a temperature of about 30° C. to about 95° C. The mixture may be stirred for about 30 minutes to about 12 hours.

The preparation method may further include the step of washing the precipitated catalyst with alcohol, after the step of precipitating the catalyst. The preparation method may further include the step of calcining the catalyst at a temperature of about 300° C. to about 600° C. for about 4 hours to about 12 hours, after washing the catalyst with alcohol.

According to still another embodiment of the present invention, a method of preparing N-substituted maleimide is provided, the method including the step of subjecting maleic anhydride and an aromatic or aliphatic primary amine to dehydrocyclization in the presence of the catalyst represented by Formula 1.

Further, a method of preparing N-substituted maleimide is provided, the method including the step of subjecting an aromatic or aliphatic monoamide of maleic acid to dehydrocyclization in the presence of the catalyst represented by Formula 1. The aromatic or aliphatic monoamide of maleic acid is a product obtained by reacting maleic anhydride with a corresponding aromatic or aliphatic primary amine, and this monoamide may be reacted without being separated from the reaction mixture.

The aromatic primary amine may be aniline, naphthylamine, toluidine, dimethylaniline, chloroaniline, dichloroaniline, hydroxyaniline, nitroaniline, or phenylenediamine. The aliphatic primary amine may be methylamine, ethylamine, propylamine, butylamine, benzylamine, cyclohexylamine, or ethylenediamine.

Effects of the Invention

A catalyst according to one embodiment of the present invention has excellent effects of minimizing formation of by-products during preparation of N-substituted maleimide to secure high catalytic activity and purity, of being reusable because its activity is not reduced even after being reused several times, and of maintaining its reaction activity for a long time.

DETAILED DESCRIPTION OF THE EMBODIMENTS

Hereinafter, a dehydration catalyst for preparing N-substituted maleimide, a preparation method thereof, and a method of preparing N-substituted maleimide using the catalyst according to a preferred embodiment of the present invention will be described in more detail.

In the present invention, the terms "first", "second", and the like are used to describe a variety of components, and these terms are merely employed to differentiate a certain component from other components.

Further, the terms used in this description are just for explaining exemplary embodiments and are not intended to restrict the present invention. Singular expressions may include plural expressions unless it is differently expressed contextually. It must be understood that the term "include", "equip", or "have" in the present description is only used for designating the existence of characteristics taken, numbers, steps, components, or combinations thereof, and does not exclude the existence or the possibility of addition of one or more different characteristics, numbers, steps, components, or combinations thereof beforehand.

The present invention may be variously modified and have various forms, and specific examples of the present invention are explained in this description. However, it is not intended to limit the present invention to the specific examples, and it must be understood that the present invention includes all modifications, equivalents, or replacements included in the spirit and technical scope of the present invention.

According to one embodiment of the present invention, a dehydration catalyst for preparing N-substituted maleimide is provided, which is represented by the following Formula 1.

$$Zr_x(H_aPO_b)_c \quad \text{[Formula 1]}$$

In Formula 1, x is 0.5 to 1.5, a and b are each independently 0 to 8, and c is 1 to 4.

For example, in the catalyst of Formula 1, c/x may be 1.5 to 2.67.

Further, the dehydration catalyst for preparing N-substituted maleimide may be represented by the following Formula 2.

$$Zr(HPO_4)_2 \quad \text{[Formula 2]}$$

In general, N-substituted maleimide may be prepared by subjecting maleic acid monoamide (maleamic acid), which is an intermediate obtained by reacting maleic anhydride with an amine, etc., to dehydrocyclization in the presence of an acid catalyst. In this regard, it is known that a phosphoric acid catalyst, a sulfuric acid catalyst, a zeolite catalyst, etc. may be used as the acid catalyst. However, use of the known acid catalysts generates a problem that 2-anilino-N-phenyl succinimide (APSI), N-(2,5-dioxo-1-phenyl-3-pyrrolidinyl)-N-phenylmaleamic acid (PPMA), maleic acid (MA), or fumaric acid (FA), and unknown polymeric materials, are produced to lower the activity of N-substituted maleimide. In particular, use of the known phosphoric acid-supported catalysts is disadvantageous in that phosphoric acid-based components, e.g., P components, contained in the catalysts are eluted in a large amount when the catalysts are reused, and as a result, activities of active sites of the catalysts are rapidly reduced and side reactions are greatly promoted. There is also a problem that the phosphoric acid-supported catalysts should be added periodically to maintain the reaction activity, in order to maintain the reaction for a long time.

It was found that the catalyst represented by Formula 1 developed in order to solve the above problems is effective in increasing purity of N-substituted maleimide and catalytic activity, and maintaining its activity for a long time even after being reused several times, thereby completing the present invention. Through the present invention, it is possible to achieve effects of producing the major by-products, APSI and PPMA, as well as other products, in smaller amounts.

The dehydration catalyst for preparing N-substituted maleimide of the present invention is characterized by an amorphous catalyst of the structure represented by Formula 1. In the catalyst of Formula 1, it is preferable that x is 0.5 to 1, a and b are each independently 0 to 4, and c is 1 to 2, in terms of remarkably improving purity of N-substituted maleimide which is obtained as a final reaction product and improving its catalytic activity, as compared with the known zirconium phosphate, etc. Particularly, in x and c of Formula 1, c/x may be in the range of 1.5 to 2.5, and preferably, in the range of 1.65 to 2.45, or 1.8 to 2.3. Hereinbelow, the zirconium phosphate catalyst represented by Formula 1 is referred to as ZrP catalyst.

Further, the acid strength and the amount of acid sites of the dehydration catalyst for preparing N-substituted maleimide of the present invention may be analyzed by $NH_3$-TPD, which is a method of desorbing ammonia gas by heating. Through $NH_3$-TPD measurement, the catalyst of the present invention may show two peaks at about 125° C. to about 145° C. and about 285° C. to about 297° C., respectively. Specifically, the peaks appearing at about 125° C. to about 145° C. may exhibit a desorption amount of 3.7 mmol to 4.2 mmol, and the peaks appearing at about 285° C. to about 297° C. may exhibit a desorption amount of 1.65 mmol to 1.95 mmol. In such a method of desorbing ammonia gas by heating, a peak appearing at a low temperature represents a weak acid strength, and a peak appearing at a high temperature represents a strong acid strength. The dehydration catalyst for preparing N-substituted maleimide of the present invention exhibits a desorption peak at a temperature of lower than about 300° C., suggesting that the acid strength of the catalyst has a medium strength.

The dehydration catalyst for preparing N-substituted maleimide of Formula 1 may have a surface area of 450 m$^2$/g or less, or 1 m$^2$/g to 450 m$^2$/g, preferably 400 m$^2$/g or less, or 3 m$^2$/g to 400 m$^2$/g, and more preferably 300 m$^2$/g or less, or 5 m$^2$/g to 300 m$^2$/g, as measured by a BET instrument. Further, the dehydration catalyst for preparing N-substituted maleimide of Formula 1 may have a pore size of about 5 nm to about 30 nm, preferably about 6 nm to about 25 nm, and more preferably about 8 nm to about 15 nm, as measured by a number average particle size. When the pore size of the catalyst is less than about 5 nm or more than about 30 nm, many side reactions may occur in the catalytic reaction, leading to a reduction in dehydration efficiency for the preparation of N-substituted maleimide.

Further, the dehydration catalyst for preparing N-substituted maleimide according to the present invention may be amorphous or crystalline, and for example, it may have an amorphous form or an orthorhombic structure, such as a pyrophosphate of $ZrP_2O_7$. Particularly, in a crystalline form with a layered structure such as the known alpha-zirconium phosphate, the reaction activity does not proceed. Therefore, it is preferable that the catalyst has a crystalline structure, other than the layered structure, or an amorphous structure.

According to another embodiment of the present invention, a method of preparing the above-described catalyst represented by Formula 1 using a precipitation method is provided. Specifically, the method of preparing the catalyst represented by Formula 1 may include the step of precipitating the catalyst of Formula 1 by mixing a zirconium precursor and a phosphate compound.

The catalyst of Formula 1 may be obtained as a precipitate only when the zirconium precursor and the phosphate compound are mixed, and therefore, a method of mixing the zirconium precursor and the phosphate compound is not particularly limited. As a non-limiting example, the precursors may be sequentially introduced into a reactor to be mixed, or may be introduced at one time to be mixed.

In the step of precipitating the catalyst, a solvent may be introduced before introducing the precursors into the reactor, and then the precursors may be introduced while stirring the solvent, or part of the precursors may be introduced into the reactor and remaining precursor may be introduced into the reactor while stirring the part of the precursors, and then a mixture of the precursors is stirred to increase a production amount of the catalyst. For example, a solvent such as water, etc. may be introduced before introducing the precursors into the reactor, and then the precursors may be sequentially or simultaneously introduced while stirring the solvent such as water, etc. For another example, part of the precursors may be first introduced into the reactor and remaining precursors may be sequentially or simultaneously introduced into the reactor while stirring the part of the precursors. For still another example, all the precursors may be sequentially or simultaneously introduced into the reactor to form a mixture, and then the mixture may be stirred.

In all of the cases, even after introducing all the precursors into the reactor, the mixture of the precursors may be continuously stirred. In particular, stirring of the mixture may be performed at a temperature of about 30° C. to about 98° C., and preferably about 35° C. to about 95° C., to further facilitate binding between metals. Further, the stirring may be performed for a sufficient time so that all of the introduced precursors are well mixed to form many precipitates. For example, the stirring may be performed for about 30 minutes to about 18 hours, preferably about 45 minutes to about 12 hours. In terms of allowing the precipitate to form well, the stirring may be performed at a stirring temperature of about 30° C. or higher and/or for a stirring time of about 30 minutes or longer, thereby preparing the catalyst with reproducibility. Further, in terms of increasing the overall process cost and efficiency, the stirring may be performed by adjusting the upper limit range of the stirring temperature and the stirring time.

The precursors used in the preparation method may employ a variety of precursors known in the art to which the present invention pertains. Non-limiting examples of the zirconium precursor may include zirconyl chloride, zirconyl bromide, zirconyl iodide, zirconyl nitrate, etc. Further, examples of the phosphate compound may include phosphoric acid, and a phosphate obtained by substituting one or more protons of phosphoric acid by cations of a Group 1 element, a Group 2 element, or a Group 13 element. The precursors may be anhydrides or hydrates. Further, the precursors may be used in a proper content according to a ratio of atoms and atomic groups of Formula 1.

In the step of precipitating the catalyst, an appropriate solvent may be used for homogeneous mixing of the precursors. The solvent is not particularly limited, and a non-limiting example thereof may include water, etc.

The preparation method may further include the step of washing the precipitated catalyst, which is obtained in the step of precipitating the catalyst, with alcohol or water, or a mixture thereof. In a precipitation method of metal compounds, a precipitate is generally washed with water. However, in one embodiment of the present invention, the precipitate is washed with alcohol, etc., thereby preparing a catalyst having a wider surface area and an optimized pore size. The catalyst having a wide surface area and an optimized pore size may exhibit more excellent catalytic activity and higher selectivity for N-substituted maleimide in the dehydration during the preparation of N-substituted maleimide.

The alcohol usable in the washing step may be exemplified by alkyl alcohols having 1 to 10 carbon atoms, such as methanol, ethanol, propanol, butanol, pentanol, hexanol, etc.

The preparation method may further include the step of calcining the catalyst obtained after performing the washing process at a temperature of about 100° C. to about 500° C. for about 4 hours to 12 hours in terms of securing high activity and mechanical property. The calcination temperature may preferably be about 100° C. to about 450° C., or about 100° C. to about 400° C., and the calcination time may preferably be about 5 hours to about 10 hours or about hours 6 to about 8 hours. That is, the calcination temperature may be about 100° C. or higher in terms of removing the precursors, and about 500° C. or lower, about 450° C. or lower, or about 400° C. or lower in terms of preventing formation of a layered structure. Further, in terms of producing the shape structure of the catalyst, the calcination time may be adjusted. In terms of removing the precursors, the calcination may be performed for about 4 hours or longer, about 5 hours or longer, or about 6 hours or longer. In terms of producing the amorphous structure, the calcination may be performed for about 12 hours or longer, about 10 hours or longer, or about 8 hours or longer.

In addition to the above-described steps, the preparation method may further include a step which is commonly employed in the art to which the present invention pertains.

According to still another embodiment of the present invention, a method of preparing N-substituted maleimide through dehydration using the catalyst prepared as above is provided.

The method of preparing N-substituted maleimide may be first exemplified by a method including the step of subjecting maleic anhydride and an aromatic or aliphatic primary amine to dehydrocyclization in the presence of the catalyst represented by the following Formula 1.

$$Zr_x(H_aPO_b)_c \qquad \text{[Formula 1]}$$

In Formula 1, x is 0.5 to 1.5, a and b are each independently 0 to 8, and c is 1 to 4.

Another example of the method of preparing N-substituted maleimide according to the present invention may be a method including the step of reacting maleic anhydride and an aromatic or aliphatic primary amine in the presence of the catalyst represented by the following Formula 1 to form maleic acid monoamide, and then effectively subjecting the maleic acid monoamide to dehydrocyclization with or without separation of the maleic acid monoamide from the reaction product.

$$Zr_x(H_aPO_b)_c \qquad \text{[Formula 1]}$$

In Formula 1, x is 0.5 to 1.5, a and b are each independently 0 to 8, and c is 1 to 4.

In the method of preparing N-substituted maleimide of the present invention, a specific composition and characteristic of the zirconium phosphate-based catalyst of Formula 1 are the same as described above.

According to the method of preparing N-substituted maleimide, maleic acid monoamide (maleamic acid), which is an intermediate obtained by reacting maleic anhydride and an aromatic or aliphatic primary amine, is subjected to dehydrocyclization in the presence of the catalyst represented by Formula 1, thereby providing N-substituted maleimide.

First, maleic anhydride which is a starting material of the present invention may be of any source, and may be appropriately selected from commercially available maleic anhydride. Maleic anhydride is usually produced by the oxidation of benzene, n-butene, or n-butane. Although the reaction proceeds in a similar manner also when maleic acid is used in place of maleic anhydride, the use of maleic acid is disadvantageous from the viewpoint of reactivity and economic efficiency.

Examples of an aromatic primary amine which is another starting material of the present invention may include aniline, naphthylamine, toluidine, dimethylaniline, chloroaniline, dichloroaniline, hydroxyaniline, nitroaniline, and phenylenediamine. Among them, aniline, toluidine, chloroaniline, dichloroaniline, hydroxyaniline, and nitroaniline are preferred. Examples of aliphatic primary amines may include methylamine, ethylamine, propylamine, butylamine, benzylamine, cyclohexylamine, and ethylenediamine. Among them, methylamine, butylamine, and cyclohexylamine are preferred.

The aromatic or aliphatic primary amine is preferably used in the range of 0.8 mol to 1.2 mol relative to 1 mol of maleic anhydride.

The dehydrocyclization of the present invention may be carried out in an organic solvent in the presence of the catalyst which has the above-described characteristics and is represented by Formula 1.

The first method of the present invention includes reacting the above-described aromatic or aliphatic primary amine and maleic anhydride in the presence of the catalyst represented by Formula 1 in an organic solvent.

Although the reaction may be carried out in various optional ways, the most preferred method from the viewpoint of operational procedures and other factors is a method including introducing maleic anhydride, a primary amine, the organic solvent, and the catalyst of Formula 1 into a reactor each in a predetermined amount and then heating them to a given temperature to effectively perform a reaction, or a method including introducing maleic anhydride, the organic solvent, and the catalyst each in a predetermined amount into a reactor, heating them to a given temperature, and then gradually adding the primary amine thereto.

The organic solvent used in the present invention may be any solvent as long as it may dissolve maleic anhydride, an aromatic or aliphatic primary amine, and maleic acid monoamide, and it should not react with the catalyst of the above formula. Preferred solvents may include aromatic hydrocarbon solvents such as benzene, toluene, xylene, ethylbenzene, styrene, and cumene. Particularly, benzene, toluene, and xylene are preferred.

An amount of the organic solvent to be used is not restricted, but from operational and economic considerations, it is preferably used in such an amount as to give a concentration of the products of about 10% to about 50%, and particularly preferably about 15% to about 35%.

Further, when a mixture of the above-mentioned aromatic hydrocarbon solvent with an aprotic polar solvent is used as the organic solvent, the reaction may be further promoted. Examples of the aprotic polar solvent may include formamide, N-methylformamide, dimethylformamide, dimethylacetamide, dimethyl sulfoxide, sulfolane, and hexamethylphosphotriamide. Among them, dimethylformamide, dimethylacetamide, and dimethyl sulfoxide are preferred.

Although the aprotic polar solvent may be used in any desired amount, it is preferably used in an amount of 50% or less, and preferably about 2% to about 30%, based on the total amount of the solvent.

In the reaction of the maleic anhydride and amine, a reaction temperature may be in the range of 50° C. to 160° C., preferably 70° C. to 140° C., from the viewpoint of the catalytic activity and thermal stability. A reaction pressure is not particularly limited. A range of the pressure may be atmospheric pressure, a reduced pressure, and an elevated pressure. A reaction time may vary depending on the concentration of the starting material, the amounts of the catalyst and the solvent, and the reaction temperature, but may be generally about 4 hours to about 6 hours, and preferably about 3 hours to about 8 hours.

The N-substituted maleimide thus formed may be easily isolated and collected by separating the catalyst from the reaction mixture by filtration and then distilling off the solvent from the filtrate.

The N-substituted maleimide may be further purified by performing distillation, recrystallization, etc. according to a general method.

The catalyst of Formula 1 useful for the method of the present invention may be reused repeatedly, and may be treated for maintenance of the catalytic activity or regeneration. Such a treatment method may include washing the catalyst with an organic solvent usable in the reaction.

The second method of the present invention may include reacting maleic anhydride with an aromatic or aliphatic primary amine in the absence of the catalyst, and then subjecting the formed maleic acid monoamide to dehydrocyclization in the presence of the catalyst of Formula 1. The dehydrocyclization step is conducted in the same manner as in the first method mentioned above. In the reaction step, the formed maleic acid monoamide may be directly subjected to dehydrocyclization without being isolated from the reaction mixture. It is possible to use, as the starting material, the maleic acid monoamide formed by reacting maleic anhydride with amine as described above.

The synthesis of maleic acid monoamide is preferably carried out in an organic solvent. The organic solvent may be an aromatic hydrocarbon solvent or mixtures thereof with aprotic polar solvents mentioned above. The reaction may be easily allowed at about 150° C. or lower, preferably at room temperature to 100° C., without using the catalyst. The reaction time may vary depending on the reaction temperature and the solvent, but is suitably in a range of about 0.5 hours to about 24 hours.

In addition to the above-described steps, the preparation method may further include a step which is commonly employed in the art to which the present invention pertains.

Meanwhile, when the catalyst of Formula 1 according to the present invention is used to perform the dehydration reaction for the preparation of N-substituted maleimide, production of by-products such as APSI, PPMA, etc. may be minimized, and the catalyst is reusable because its activity is not reduced even after being reused several times, and thus the reaction activity may be maintained for a long time. First, when the catalyst of Formula 1 is used once to perform the dehydration reaction for the preparation of N-substituted maleimide, the reaction product may show a conversion ratio of primary amine of about 100%, and selectivity for produced N-substituted maleimide of about 80% or more, preferably about 83% or more, and more preferably about 85% or more. Further, when the catalyst of Formula 1 is used consecutively twice or more to perform the dehydration reaction for the preparation of N-substituted maleimide, the reaction product may show a conversion ratio of primary amine of about 100%, and selectivity for produced N-substituted maleimide of about 75% or more, preferably about 78% or more, and more preferably about 80% or more. Particularly, when the catalyst of Formula 1 is used consecutively three times or more to perform the dehydration reaction for the preparation of N-substituted maleimide, the reaction product may show a conversion ratio of primary amine of about 99% or more, and selectivity for produced N-substituted maleimide of about 60% or more, preferably about 65% or more, and more preferably about 70% or more. As such, even after the catalyst is repeatedly reused twice or three times or more, a content of the phosphoric acid-based component remaining in the catalyst may be about 80% by weight or more, preferably about 85% by weight or more, and more preferably about 95% by weight or more, based on the content before use in the reaction. That is, even after the dehydration catalyst for preparing N-substituted maleimide of the present invention is used consecutively at least twice or three times or more to perform the dehydration reaction, loss of the phosphoric acid-based component in the catalyst is merely about 20% by weight or less, preferably about 15% by weight or less, and more preferably about 5% by weight or less, as compared with the content before initial injection for dehydration, indicating that the catalyst continues to maintain excellent activity.

Hereinafter, preferred examples will be provided for better understanding of the present invention. However, the following examples are provided only for understanding the present invention more easily, and the content of the present invention is not limited thereby.

Example 1

Preparation of Dehydration Catalyst ZrP for Preparing N-Substituted Maleimide 12.208 g of $ZrOCl_2$ as a zirconium precursor was added to 300 mL of distilled water to prepare an aqueous solution. 8.714 g of $NH_4H_2PO_4$ as a phosphate precursor was added to the aqueous solution. The aqueous solution was stirred at a temperature of about 95° C. overnight.

Thereafter, a precipitate precipitated from the aqueous solution was washed with ethanol, and calcined at 400° C. for 8 hours to obtain a zirconium phosphate catalyst (ZrP) represented by the following Formula 2 as a dehydration catalyst for preparing N-substituted maleimide. Acid strength of the ZrP catalyst thus obtained was measured by ammonia temperature-programmed desorption ($NH_3$-TPD), and as a result, a peak at about 130° C. (desorption: 4.04 mmol) and a peak at about 292° C. (desorption: 1.835 mmol) were observed. Further, surface area of the ZrP catalyst was measured by a BET method, and as a result, the ZrP catalyst had a surface area of about 250 $m^2$/g and mesopores having a pore size of 14.8 nm.

$$Zr(HPO_4)_2 \qquad \text{[Formula 2]}$$

Preparation of N-Substituted Maleimide

In the presence of the dehydration catalyst ZrP for preparing N-substituted maleimide obtained as above, a dehydrocyclization reaction was performed at 135° C. for 6 hours using maleic anhydride (MAH), aniline (ANL), and O-xylene as a solvent to obtain a product N-phenyl maleimide (PMI), which was analyzed by gas chromatography (GC) and liquid chromatography (LC).

The dehydrocyclization reaction was performed under conditions of a mole ratio of MAH/ANL=1.1, a total solid content of about 30%, a reaction temperature of 135° C., and a reaction time of 6 hours. After the dehydrocyclization reaction was completed once (Example 1-1), the used catalyst was washed with O-xylene, and then dried and reused to perform the reaction again (Example 1-2) and a third time (Example 1-3). Each product of the reactions was subjected to GC and LC analysis in the same manner as in the one-time reaction (Example 1-1).

Example 2

Preparation of Dehydration Catalyst ZrP for Preparing N-Substituted Maleimide 14.601 g of zirconium oxynitrate hydrate ($ZrO(NO_3)_2 \cdot XH_2O$) as a zirconium precursor was added to 300 mL of distilled water to prepare an aqueous solution. 10.564 g of $NH_4H_2PO_4$ as a phosphate precursor was added to the aqueous solution. The aqueous solution was stirred at a temperature of about 95° C. overnight.

Thereafter, a precipitate precipitated from the aqueous solution was washed with ethanol or water, and calcined at 100° C. for 8 hours to obtain a zirconium phosphate catalyst (ZrP) represented by the following Formula 2 as a dehydration catalyst for preparing N-substituted maleimide. Acid strength of the ZrP catalyst thus obtained was measured by ammonia temperature-programmed desorption ($NH_3$-TPD), and as a result, a peak at about 130° C. (desorption: 4.04 mmol) and a peak at about 292° C. (desorption: 1.835 mmol) were observed. Further, the surface area of the ZrP catalyst was measured by a BET method, and as a result, the ZrP catalyst had a surface area of about 2.93 $m^2$/g and mesopores having a pore size of 24.3 nm.

$$Zr(HPO_4)_2 \quad \text{[Formula 2]}$$

Preparation of N-Substituted Maleimide

In the presence of the dehydration catalyst ZrP for preparing N-substituted maleimide obtained as above, a dehydrocyclization reaction was performed at 135° C. for 6 hours using maleic anhydride (MAH), aniline (ANL), and O-xylene as a solvent to obtain a product N-phenyl maleimide (PMI), which was analyzed by gas chromatography (GC) and liquid chromatography (LC).

The dehydrocyclization reaction was performed under conditions of a mole ratio of MAH/ANL=1.1, a total solid content of about 30%, a reaction temperature of 135° C., and a reaction time of 6 hours. After the dehydrocyclization reaction was completed once (Example 2-1), the used catalyst was washed with O-xylene, and then dried and reused to perform the reaction again (Example 2-2) and a third time (Example 2-3). Each product of the reactions was subjected to GC and LC analysis in the same manner as in the one-time reaction (Example 2-1).

Comparative Example 1

Preparation of Dehydration Catalyst of 20 wt % $H_3PO_4$/$SiO_2$ for Preparing N-Substituted Maleimide 20 g of a $SiO_2$ carrier (product name: SP952X) was added to 150 mL of distilled water to prepare an aqueous solution. $H_3PO_4$ as a phosphate compound was added to the aqueous solution. The aqueous solution was stirred at a temperature of about 50° C. to 80° C. for 1 hour.

After stirring, ethanol was removed therefrom by using a rotary evaporator under conditions of high temperature and reduced pressure to obtain a solid. This solid was dried in an oven overnight, and then calcined at 150° C. for 8 hours to obtain 20 wt % of $H_3PO_4$/$SiO_2$ which is a dehydration catalyst for preparing N-substituted maleimide.

Preparation of N-Substituted Maleimide

The dehydrocyclization reaction was performed in the same manner as in Example 1, except for using 20 wt % of $H_3PO_4$/$SiO_2$ which is the dehydration catalyst for preparing N-substituted maleimide obtained as above. The dehydrocyclization reaction was performed once (Comparative Example 1-1), twice (Comparative Example 1-2), and three times (Comparative Example 1-3). Each product was subjected to GC and LC analysis.

Comparative Example 2

Preparation of Dehydration Catalyst of 1.5 wt % P/$Si_2$ for Preparing N-Substituted Maleimide 20 g of a $SiO_2$ carrier (product name: SP952X) was added to 150 mL of distilled water to prepare an aqueous solution. $H_3PO_4$ as a phosphate compound was added to the aqueous solution. The aqueous solution was stirred at a temperature of about 50° C. to 80° C. for 1 hour.

After stirring, ethanol was removed therefrom by using a rotary evaporator under conditions of high temperature and reduced pressure to obtain a solid. This solid was dried in an oven overnight, and then calcined at 700° C. for 8 hours to obtain 1.5 wt % of P/$SiO_2$ which is a dehydration catalyst for preparing N-substituted maleimide.

Preparation of N-Substituted Maleimide

The dehydrocyclization reaction was performed in the same manner as in Example 1, except for using 1.5 wt % of P/$SiO_2$ which is the dehydration catalyst for preparing N-substituted maleimide obtained as above. The dehydrocyclization reaction was performed once (Comparative Example 2-1) and twice (Comparative Example 2-2). Each product was subjected to GC and LC analysis.

Results of analyzing the products resulting from the preparation reaction of N-substituted maleimide according to Examples 1 to 2 and Comparative Examples 1 to 2 are as shown in the following Table 1.

TABLE 1

|  | Kind of catalyst | Number of reaction | ANL Conv. | PMI Sel. | PMA Sel. | APSI Sel. | PPMA Sel. | Others Sel. |
|---|---|---|---|---|---|---|---|---|
| Example 1-1 | $Zr(HPO_4)_2$ | 1 | 100 | 88.5 | 1.2 | 2.1 | 0.9 | 7.3 |
| Example 1-2 | $Zr(HPO_4)_2$ | 2 | 100 | 82.8 | 2.1 | 3.5 | 1.3 | 9.4 |
| Example 1-3 | $Zr(HPO_4)_2$ | 3 | 99.2 | 71.5 | 11.2 | 2.2 | 0.9 | 14.2 |
| Example 2-1 | $Zr(HPO_4)_2$ | 1 | 100 | 91.45 | 0.85 | 0.70 | 0.05 | 6.95 |
| Example 2-2 | $Zr(HPO_4)_2$ | 2 | 100 | 87.38 | 1.14 | 1.06 | 0.31 | 9.07 |
| Example 2-3 | $Zr(HPO_4)_2$ | 3 | 100 | 81.52 | 6.78 | 1.00 | 0.45 | 10.25 |
| Comparative Example 1-1 | 20 wt % $H_3PO_4$/$SiO_2$ | 1 | 100 | 86.1 | 1.3 | 2.5 | 1.0 | 9.2 |
| Comparative Example 1-2 | 20 wt % $H_3PO_4$/$SiO_2$ | 2 | 100 | 77.1 | 3.3 | 2.8 | 1.3 | 15.5 |
| Comparative Example 1-3 | 20 wt % $H_3PO_4$/$SiO_2$ | 3 | 99.8 | 10.9 | 2.9 | 0.3 | 0.1 | 85.7 |
| Comparative Example 2-1 | 1.5 wt % P/$SiO_2$ | 1 | 100 | 91.9 | 1.9 | 3.9 | 1.49 | 0.7 |
| Comparative Example 2-2 | 1.5 wt % P/$SiO_2$ | 2 | 100 | 37.1 | 0.02 | 0.01 | 0.04 | 62.8 |

ANL Conv (aniline conversion ratio) = amount of reacted aniline/amount of injected aniline
Selectivity (based on aniline) = amount of desired product/total amount of product produced during reaction
APSI: 2-anilino-N-phenyl succinimide
PMA: N-phenyl maleamic acid
PPMA: N-(2,5-dioxo-1-phenyl-3-pyrrolidinyl)-N-phenylmaleamic acid
Others: other by-products Further, before performing the preparation of N-substituted maleimide and after performing the preparation of N-substituted maleimide three times using each of the catalysts prepared according to Example 1 and Comparative Example 1 as described above, the content of the phosphoric acid-based component in the catalyst was analyzed by ICP analysis. The content of the phosphoric acid-based component in the catalysts of Example 1 and Comparative Example 1 before and after reaction was analyzed by Inductively Coupled Plasma (ICP) analysis, and the results are as shown in the following Table 2.

TABLE 2

| | Comparative Example 1 | Example 1 |
|---|---|---|
| Composition of catalyst | $H_3PO_4/SiO_2$ | $Zr(HPO_4)_2$ |
| Content of phosphoric acid-based component in catalyst, before reaction (wt %) | 3.63 | 10.40 |
| Content of phosphoric acid-based component in catalyst, after reaction (wt %) | 2.70 | 10.03 |

As shown in Table 1, Examples 1 and 2 which are the dehydration catalysts for preparing N-substituted maleimide according to the present invention were found to produce smaller amounts of major by-products, APSI and PPMA, and other by-products (others). In particular, even after being reused three times or more, the zirconium phosphate-based catalysts of Examples 1 and 2 according to the present invention showed no loss of P, although water was generated, and maintained their catalytic activities even after being reused. Specifically, Examples 1 and 2 showed excellent selectivity for N-substituted maleimide (PMI) of 71.5% and 81.52%, respectively, even after being used consecutively three times or more.

As shown in Table 2, loss of the phosphoric acid-based component (P) before and after reaction was examined through ICP analysis of the catalysts of Example 1 and Comparative Example 1. As a result, the phosphoric acid-supported catalyst of Comparative Example 1 showed a P loss of about 25% or more after reaction, and the $Zr(HPO_4)_2$ catalyst which is the ZrP catalyst of Example 1 according to the present invention showed a P loss of less than about 5% after reaction, indicating that P loss hardly occurred.

Moreover, it can be seen that Comparative Examples 1 and 2 using the catalyst according to the known method had remarkably lowered catalytic activities and produced very large amounts of by-products such as APSI and PPMA. In particular, when the known phosphoric acid-supported catalyst of Comparative Example 1 was reused several times, its catalytic activity was reduced, because the phosphoric acid component P was dissolved in water generated by dehydration during reaction, resulting in P loss. Further, it is considered that since the calcination temperature of the phosphoric acid-supported catalyst was 150° C., P was not stably bound and thus P loss occurred. When the catalyst of Comparative Example 2 prepared at the calcination temperature of 700° C. was used, its catalytic activity was rapidly reduced after being reused.

The invention claimed is:

1. A dehydration catalyst for preparing N-substituted maleimide represented by the following Formula 1:

$$Zr_x(H_aPO_b)_c \quad \text{[Formula 1]}$$

wherein, in Formula 1, x is 0.5 to 1.5, a and b are each independently 0 to 8, and c is 1 to 4.

2. The dehydration catalyst for preparing N-substituted maleimide of claim 1, wherein c/x is 1.5 to 2.67.

3. A method of preparing a dehydration catalyst for preparing N-substituted maleimide, comprising the step of precipitating a catalyst represented by the following Formula 1 by mixing a zirconium precursor and a phosphate compound:

$$Zr_x(H_aPO_b)_c \quad \text{[Formula 1]}$$

wherein, in Formula 1, x is 0.5 to 1.5, a and b are each independently 0 to 8, and c is 1 to 4.

4. The method of preparing the dehydration catalyst for preparing N-substituted maleimide of claim 3, wherein the step of precipitating the catalyst includes stirring the mixture containing the zirconium precursor and the phosphate compound at a temperature of 30° C. to 98° C.

5. The method of preparing the dehydration catalyst for preparing N-substituted maleimide of claim 4, wherein the mixture is stirred for 30 minutes to 18 hours.

6. The method of preparing the dehydration catalyst for preparing N-substituted maleimide of claim 3, further comprising the step of washing the precipitated catalyst with alcohol or water or a mixture thereof, after the step of precipitating the catalyst.

7. The method of preparing the dehydration catalyst for preparing N-substituted maleimide of claim 6, further comprising the step of calcining the catalyst at a temperature of 100° C. to 500° C. for 4 hours to 12 hours, after washing the catalyst with alcohol or water or a mixture thereof.

8. A method of preparing N-substituted maleimide, comprising the step of subjecting maleic anhydride and an aromatic or aliphatic primary amine to dehydrocyclization, or an aromatic or aliphatic monoamide of maleic acid to dehydrocyclization, in the presence of a catalyst represented by the following Formula 1:

$$Zr_x(H_aPO_b)_c \quad \text{[Formula 1]}$$

wherein, in Formula 1, x is 0.5 to 1.5, a and b are each independently 0 to 8, and c is 1 to 4.

9. The method of preparing N-substituted maleimide of claim 8, wherein the aromatic primary amine is aniline, naphthylamine, toluidine, dimethylaniline, chloroaniline, dichloroaniline, hydroxyaniline, nitroaniline, or phenylenediamine.

10. The method of preparing N-substituted maleimide of claim 8, wherein the aliphatic primary amine is methylamine, ethylamine, propylamine, butylamine, benzylamine, cyclohexylamine, or ethylenediamine.

11. The method of preparing N-substituted maleimide of claim 8, wherein the aromatic or aliphatic monoamide of maleic acid is a product obtained by reacting maleic anhydride with a corresponding aromatic or aliphatic primary amine, and this monoamide is reacted without being separated from the reaction mixture.

12. The method of preparing N-substituted maleimide of claim 11, wherein the aromatic primary amine is aniline, naphthylamine, toluidine, dimethylaniline, chloroaniline, dichloroaniline, hydroxyaniline, nitroaniline, or phenylenediamine.

13. The method of preparing N-substituted maleimide of claim 11, wherein the aliphatic primary amine is methylamine, ethylamine, propylamine, butylamine, benzylamine, cyclohexylamine, or ethylenediamine.

* * * * *